(12) United States Patent
Fakhouri et al.

(10) Patent No.: US 9,987,009 B2
(45) Date of Patent: Jun. 5, 2018

(54) PNEUMATIC ACTUATOR FOR DISPENSING SURGICAL STAPLES

(71) Applicant: KING SAUD UNIVERSITY, Riyadh (SA)

(72) Inventors: Faisal Saud Fakhouri, Riyadh (SA); Abdulaziz Saud Fakhouri, Riyadh (SA); Justo Juvian Torres-Rodriguez, Columbus, OH (US)

(73) Assignee: KING SAUD UNIVERSITY, Riyadh (SA)

( * ) Notice: Subject to any disclaimer, the term of this patent is extended or adjusted under 35 U.S.C. 154(b) by 0 days. days.

(21) Appl. No.: 15/729,515

(22) Filed: Oct. 10, 2017

(65) Prior Publication Data

US 2018/0028183 A1 Feb. 1, 2018

Related U.S. Application Data

(63) Continuation-in-part of application No. 15/473,576, filed on Mar. 29, 2017.

(60) Provisional application No. 62/314,605, filed on Mar. 29, 2016.

(51) Int. Cl.
*B25C 1/04* (2006.01)
*A61B 17/072* (2006.01)
*A61B 17/00* (2006.01)

(52) U.S. Cl.
CPC ............. *A61B 17/07207* (2013.01); *A61B 2017/00544* (2013.01); *A61B 2017/07278* (2013.01)

(58) Field of Classification Search
CPC ..... B27F 7/34; B25C 5/13; B25C 1/04; B25C 1/041–1/043; B25C 1/047
See application file for complete search history.

(56) References Cited

U.S. PATENT DOCUMENTS

| 3,067,724 | A | * | 12/1962 | Jenny | B25C 1/041 173/169 |
| 3,191,841 | A | * | 6/1965 | Schafroth | B25C 1/041 227/108 |
| 4,938,408 | A | * | 7/1990 | Bedi | A61B 17/072 227/130 |
| 5,005,754 | A | * | 4/1991 | Van Overloop | A61B 17/072 227/178.1 |
| 6,619,529 | B2 | * | 9/2003 | Green | A61B 17/07207 227/176.1 |

(Continued)

*Primary Examiner* — Andrew M Tecco
(74) *Attorney, Agent, or Firm* — Richard C. Litman

(57) ABSTRACT

The pneumatic actuator for dispensing surgical staples is a handheld actuator for use with a typical staple cartridge. A source of pressurized fluid is used to automatically drive forward movement of a plunger rod. As in a conventional, manually-driven surgical stapler, the forward movement of the plunger rod is used to actuate the surgical stapler to bend and eject a staple. The pneumatic actuator may be used with any suitable type of surgical staple cartridge, through coupling of the plunger rod thereto. The pneumatic actuator for dispensing surgical staples includes a housing having an upper portion, for receiving the pressurized fluid to drive the plunger rod, and a lower portion, which is configured to act as a gripping handle for the user. A finger-actuated trigger is further provided, allowing for single finger release of the pressurized fluid to reset the pneumatic actuator for a surgical stapler.

4 Claims, 6 Drawing Sheets

(56) References Cited

U.S. PATENT DOCUMENTS 8,603,102 B2 * 12/2013 Lozier .................. A61B 17/068
606/104
2005/0247750 A1 * 11/2005 Burkholder ............... B25C 1/04
227/130

* cited by examiner

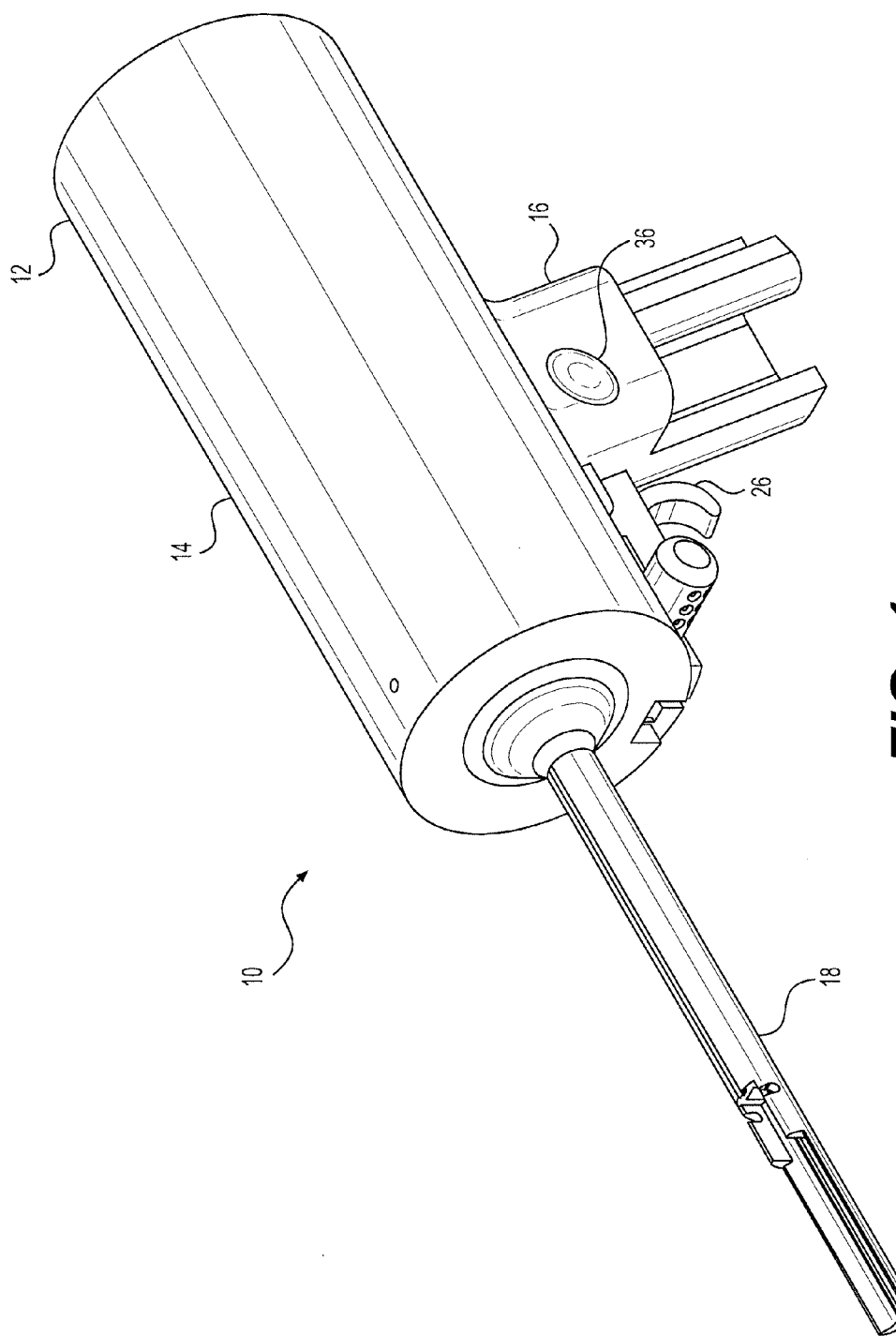

PNEUMATIC ACTUATOR FOR DISPENSING SURGICAL STAPLES

CROSS-REFERENCE TO RELATED APPLICATION

This application is a continuation-in-part of U.S. patent application Ser. No. 15/473,576, filed on Mar. 29, 2017, which claimed the benefit of U.S. Provisional Patent Application Ser. No. 62/314,605, filed on Mar. 29, 2016.

BACKGROUND

1. Field

The present invention relates to medical devices, and particularly to a pneumatic actuator for a surgical stapler.

2. Description of the Related Art

FIGS. 2A and 2B show a typical, prior art surgical stapler. As shown, surgical stapler 100 includes a housing or casing 140, with a rear portion 102 thereof being substantially tubular and having a handle 103 extending downwardly therefrom. A front end 104 of rear portion 102 is tapered for receiving a rear end 105 of a smaller diameter, front portion 106 of casing 140. As shown, front portion 106 and rear portion 102 define an elongated barrel for slidably supporting a plunger 107. A control sleeve 108 is rotatably mounted on one end of the plunger 107. The plunger 107 and the sleeve 108 are biased to the rest position (shown in the configuration of FIG. 2A) by a helical spring 111. The spring 111 is mounted on the plunger 107 and extends between an internal shoulder 112 near the tapered end of the rear portion 102 of the casing 140 and a sleeve 113, which is fixedly mounted on the plunger 107 in front of the control sleeve 108. The sleeve 113 includes a rear flange 114, extending radially inwardly for retaining the spring 111.

A trigger 115 is pivotally connected to the casing 140 in front of the handle 103 for rotation around a screw 116. The end of the trigger 115 within the casing 140 is bifurcated, with the two arms thereof defining lugs 117 (only one is shown for purposes of simplification), which lie on either side of the plunger 107 within a gap between the front end of the sleeve 108 and the rear end of the sleeve 113. When the trigger 115 is squeezed towards the handle 103, the lugs 117 press against the rear end of the sleeve 113 to move the plunger 107 forwardly, compressing the spring 111.

When the stapler 100 is put into an operative state, the plunger 107 can be moved forward a distance sufficient to discharge a staple from a staple cartridge. As shown in FIGS. 2A and 2B, the plunger 107 is defined by an elongated rod with a threaded hole 128 for securing the rear end of plunger 107 to casing 140 by a threaded screw or the like. The outer or front end of the plunger 107 is flared slightly and cut away to define a shoulder 132, which bears against a staple 133 when the staple 133 is placed on a support surface 34 at the front end of the casing 140.

The leading edge 135 of the casing 140 includes a shoulder which defines a generally V-shaped anvil for deforming the staple 133 in conjunction with a post 137. When the plunger 107 is forced forwardly, arms of the staple 133 are deformed by the anvil to define a tight loop, similar to the bending or folding of a conventional staple. As noted above, in order to actuate the surgical stapler, the surgeon must squeeze trigger 115 towards handle 103. Given the delicate and precise nature of surgical procedures, the manual force required to actuate the surgical stapler via trigger 115 could cause the surgeon's hand to slightly move or shake, resulting in misplacement of the staple and/or injury to the patient. Similarly, the mechanical shock generated by the sudden thrust forward of plunger 107 could cause the surgical stapler to move or vibrate in the surgeon's hand. Thus, a pneumatic actuator for dispensing surgical staples solving the aforementioned problems are desired.

SUMMARY

The pneumatic actuator for dispensing surgical staples is a handheld actuator for use with a surgical stapler. A source of pressurized fluid is used to automatically drive forward movement of a plunger rod. As in a conventional, manually-driven surgical stapler, the forward movement of the plunger rod is used to actuate the surgical stapler to bend and eject a staple, and the pneumatic actuator for dispensing surgical staples may be used with any suitable type of surgical stapler, through coupling of the plunger rod thereto.

The pneumatic actuator includes a housing having an upper portion, a central portion and a lower portion. A longitudinally extending hollow chamber is formed in the upper portion of the housing and a flow passage is formed in the central portion of the housing. The lower portion of the housing is adapted for gripping by the hand of a surgeon or other medical practitioner. A feed line is at least partially mounted within the lower portion of the housing for receiving pressurized fluid from an external source, such as a tank of pressurized fluid, an air compressor or the like. The feed line is in selective fluid communication with the flow passage formed in the central portion of the housing, with a first valve selectively controlling the flow of the pressurized fluid from the feed line to the flow passage formed in the central portion of the housing. A button, knob or the like is preferably mounted on the lower portion of the housing and is mechanically coupled to the first valve for selective opening and closing thereof.

A piston is slidably received in the longitudinally extending hollow chamber, dividing the longitudinally extending hollow chamber into a front portion and a rear portion. The piston provides a fluid-tight seal between the front portion and the rear portion and is elastically biased against a front wall of the upper portion of the housing. The flow passage is in open fluid communication with the rear portion of the longitudinally extending hollow chamber. A guide tube is mounted to the front wall of the upper portion of the housing and extends longitudinally therefrom. A plunger rod is secured to the piston and extends longitudinally to be at least partially received by, and slidably supported within, the guide tube.

In use, the user selectively opens the first valve such that the pressurized fluid flows through the flow passage formed in the central portion of the housing and into the rear portion of the longitudinally extending hollow chamber to urge the piston forwardly therein. The forward movement of the piston pushes the plunger rod forwardly within the guide tube, and the plunger rod is adapted for actuation of a surgical stapler upon its forward movement.

These and other features of the present invention will become readily apparent upon further review of the following specification.

BRIEF DESCRIPTION OF THE DRAWINGS

FIG. 1 is a perspective view of a pneumatic actuator for a surgical stapler.

Similar reference characters denote corresponding features consistently throughout the attached drawings.

DETAILED DESCRIPTION OF THE PREFERRED EMBODIMENTS

Figure 2A:
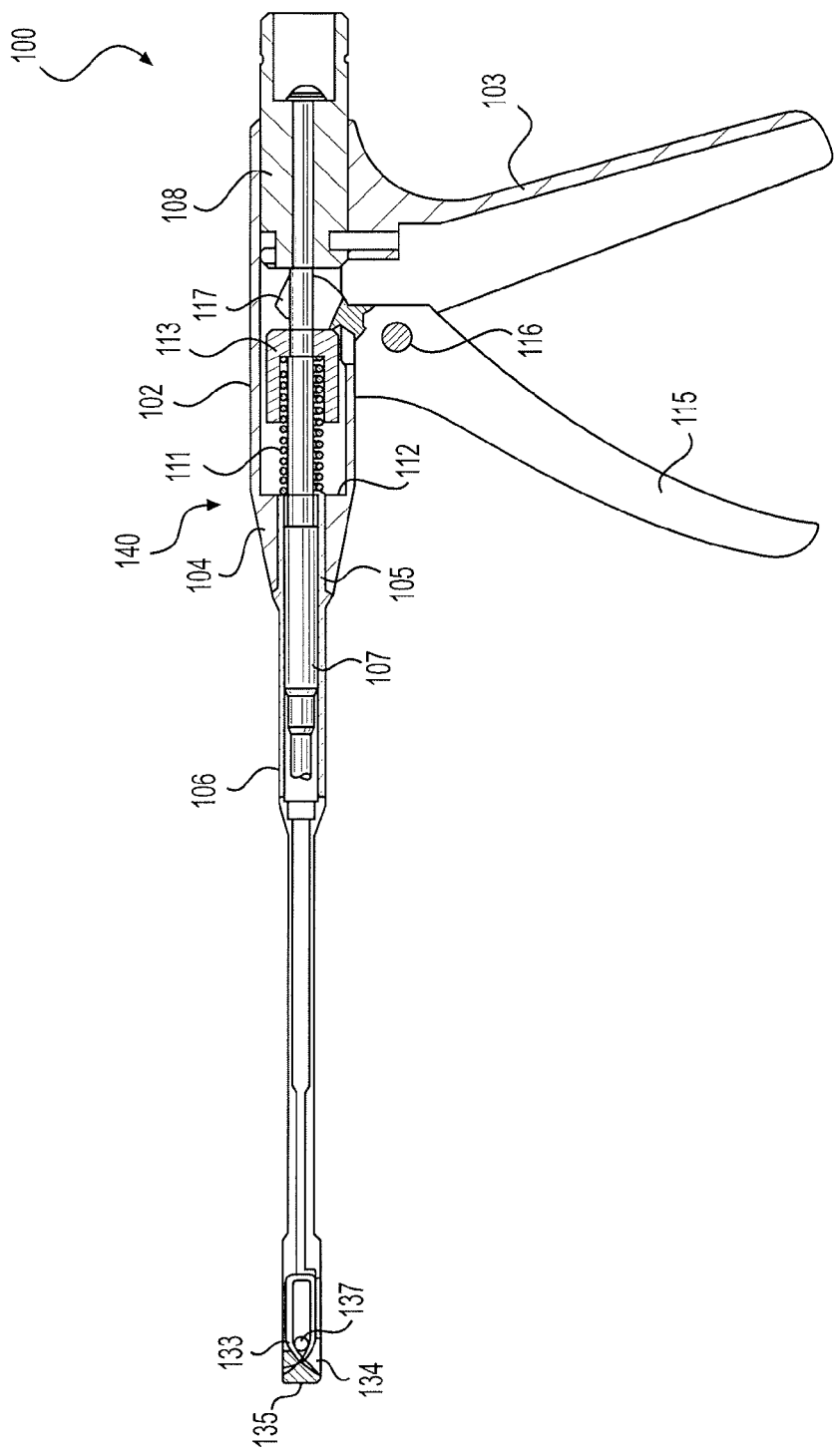
FIG. 2A is a side view in section of a prior art surgical stapler.
Figure 2B:
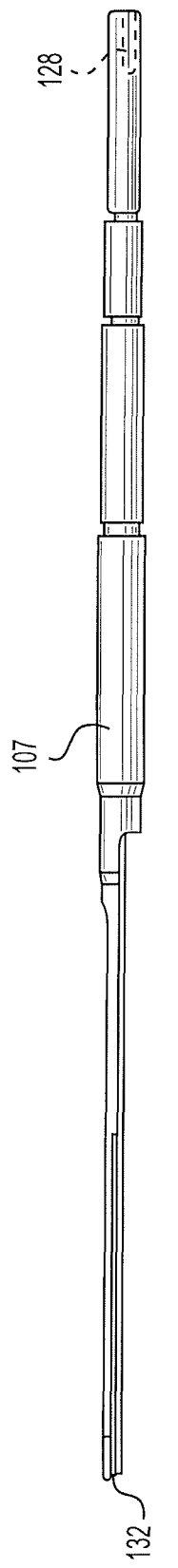
FIG. 2B is a side view a plunger of the prior art surgical stapler of FIG. 2A.

The pneumatic actuator for dispensing surgical staples 10 is a handheld actuator for dispensing surgical staples. The pneumatic actuator 10 can be configured to include or be removably attached to any suitable staple cartridge, e.g., a staple cartridge including surgical staples and knife. A source of pressurized fluid, such as exemplary pressurized gas G (e.g., $CO_2$) is used to automatically drive forward movement of a plunger rod 20. As in a conventional, manually-driven surgical stapler, such as that shown in FIGS. 2A and 2B, the forward movement of the plunger rod 20 is used to actuate the staple cartridge to eject a staple which then slices and staples tissue in a conventional manner. It should be understood that the pneumatic actuator for dispensing surgical staples 10 may be used with any suitable type of staple cartridge through suitable coupling of the plunger rod 20 thereto.

Figure 3A:
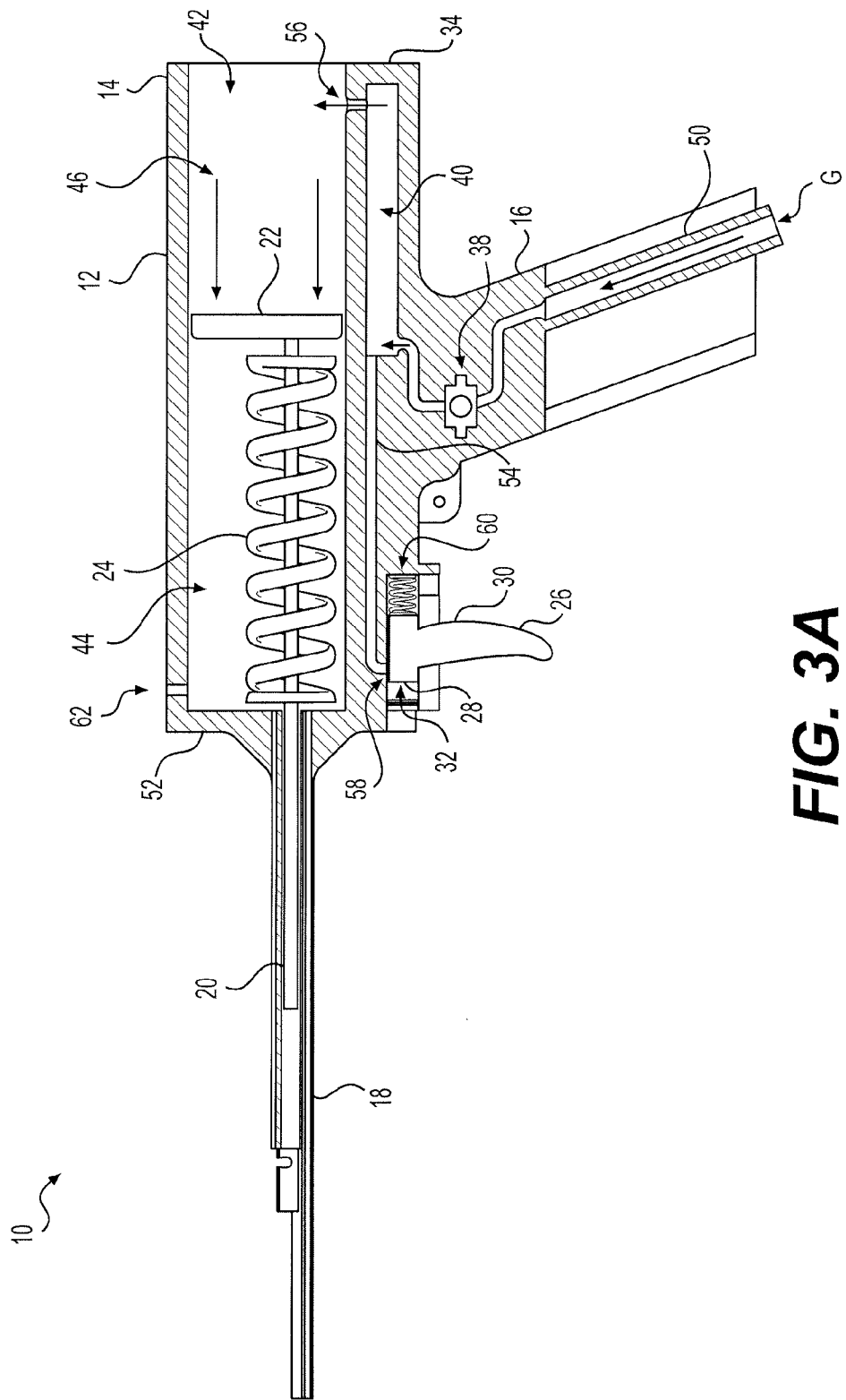
FIG. 3A is a side view in section of the pneumatic actuator for a surgical stapler.

As best seen in FIG. 3A, the pneumatic actuator for dispensing surgical staples 10 includes a housing 12 having an upper portion 14, a central portion 34 and a lower portion 16. A longitudinally extending hollow chamber 42 is formed in the upper portion 14 of the housing 12, and a flow passage 40 is formed in the central portion 34 of housing 12. The lower portion 16 of the housing 12 is adapted for gripping by the hand of a surgeon or other medical practitioner. A feed line 50 is at least partially mounted within the lower portion 16 of housing 12 for receiving pressurized fluid (such as exemplary pressurized gas G) from an external source, such as a tank of pressurized fluid, an air compressor or the like. The feed line 50 is in selective fluid communication with the flow passage 40 formed in the central portion 34 of housing 12, with a first valve 38 selectively controlling the flow of the pressurized fluid from the feed line 50 to the flow passage 40 formed in the central portion 34 of housing 12. As shown in FIG. 1, a knob 36, button or the like is preferably mounted on the lower portion 16 of the housing 12 and is mechanically coupled to the first valve 38 for selective opening and closing of the valve 38. The user may adjust the knob, as desired, to regulate or control the amount of pressure in the chamber 42.

A piston 22 is slidably received in the longitudinally extending hollow chamber 42, dividing the longitudinally extending hollow chamber 42 into a front portion 44 and a rear portion 46. The piston 22 provides a fluid-tight seal between the front portion 44 and the rear portion 46 and is elastically biased against a front wall 52 of the upper portion 14 of housing 12 by a spring 24 or the like. The flow passage 40 is in open fluid communication with the rear portion 46 of the longitudinally extending hollow chamber 42 (through port 56). A guide tube 18 is mounted to the front wall 52 of the upper portion 14 of housing 12 and extends longitudinally therefrom. A plunger rod 20 is secured to the piston 22 and extends longitudinally to be at least partially received by, and slidably supported within, the guide tube 18, as shown.

Figure 3B:
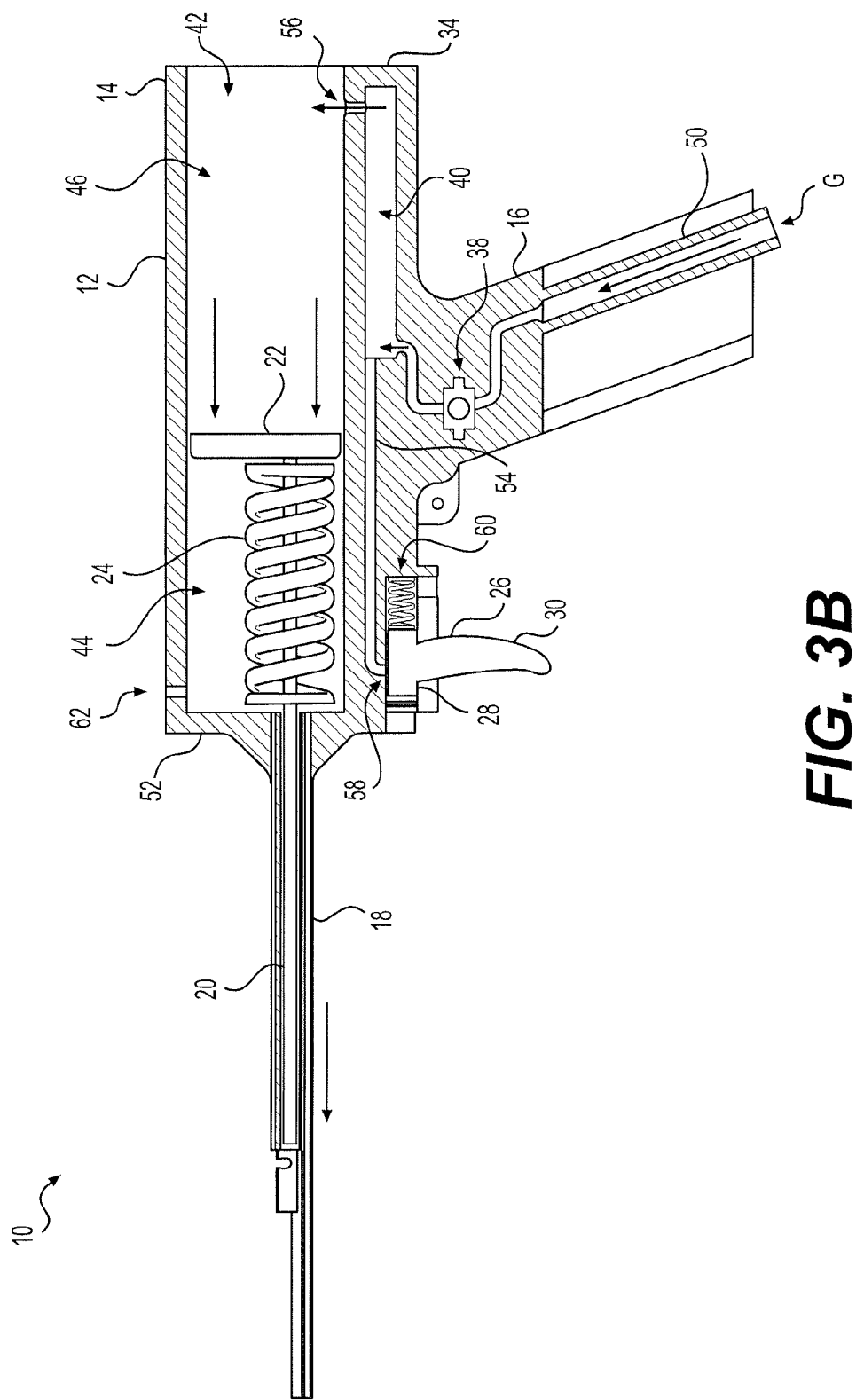
FIG. 3B is a side view in section of the pneumatic actuator for a surgical stapler, shown in a partially actuated configuration.

In use, as shown in FIGS. 3A and 3B, the user selectively opens the first valve 38 (via actuation of knob 36 of FIG. 1) such that the pressurized fluid (here shown as exemplary pressurized gas G) flows from feed line 50, through the flow passage 40 formed in the central portion 34 of housing 12, and into the rear portion 46 of the longitudinally extending hollow chamber 42. The pressurized fluid entering rear portion 46 urges the piston 22 forwardly within hollow chamber 42. The forward movement of the piston 22 pushes the plunger rod 20 forwardly within the guide tube 18 (FIG. 3B), and the plunger rod 20 is adapted for actuation of a surgical staple cartridge upon its forward movement. It should be understood that the knob 36 may be used to regulate the pressure in the rear portion 46, as desired, e.g., to adjust pressure depending on the thickness of the tissue that is to be stapled.

Following the stapling operation, the user actuates a second valve for selectively releasing the pressurized fluid from the rear portion 46 of the longitudinally extending hollow chamber 42. As shown in FIGS. 1 and 3A-3C, the second valve is preferably in the form of a finger-actuated trigger 26, allowing for single-finger release of the pressurized fluid to reset the piston 22, without the user having to release his or her grip in the lower portion 16 of housing 12.

Figure 3C:
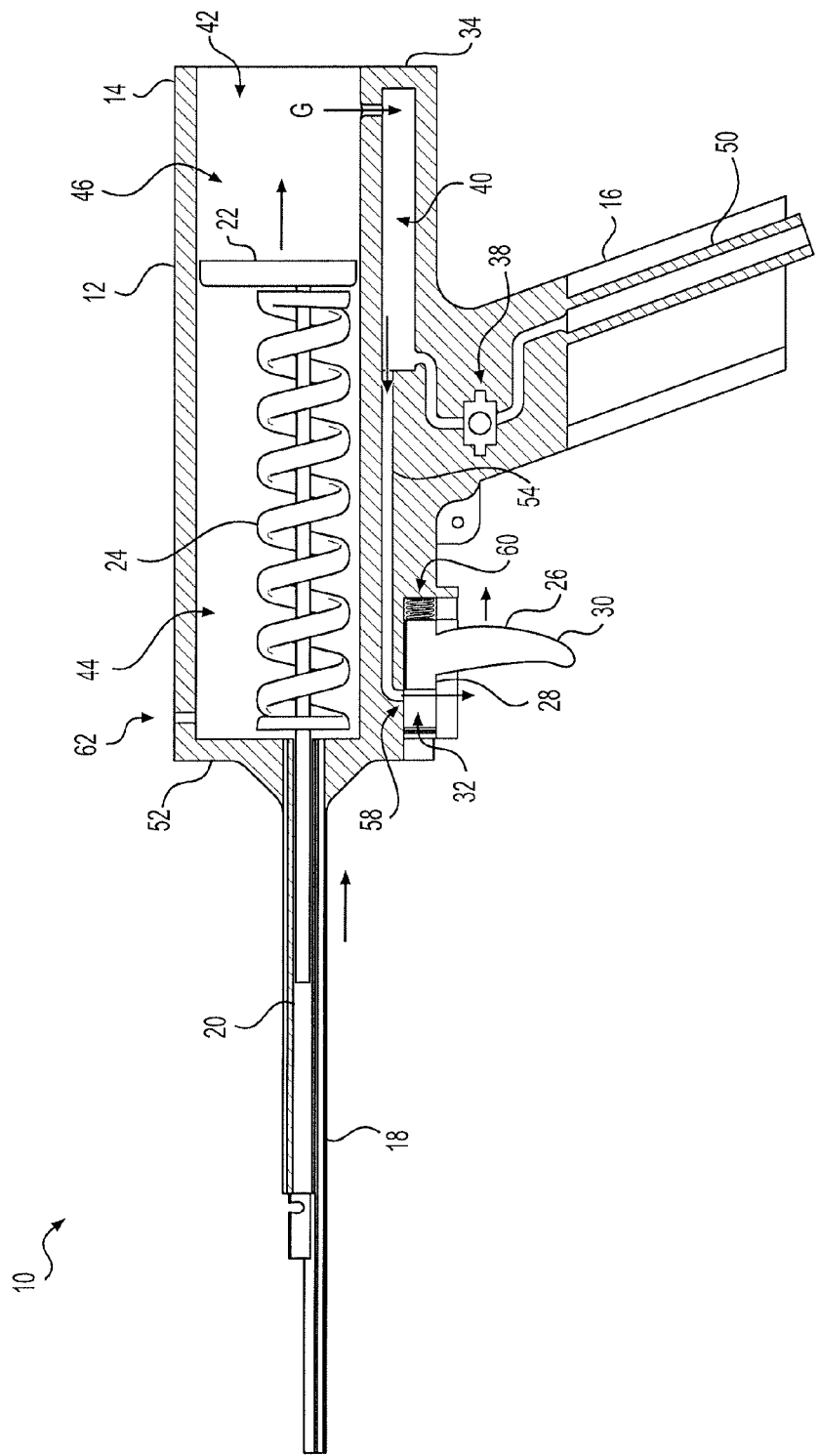
FIG. 3C is a side view in section of the pneumatic actuator for a surgical stapler, shown in a partially released configuration.

As best seen in FIGS. 3A-3C, an upper portion 28 of the finger-actuated trigger 26 is slidably received within a trigger chamber 32 formed in the central portion 34 of housing 12. A release conduit 54 extends between the flow passage 40 and the trigger chamber 32, such that the release conduit 54 is in fluid communication with the trigger chamber 32 through a port 58. The upper portion 28 of the finger-actuated trigger 26 selectively seals the port 58. As shown, the upper portion 28 of the finger-actuated trigger 26 is elastically biased within the trigger chamber 32 by spring 60 or the like.

Thus, as shown in FIG. 3C, in use, following stapling, in order to reset the piston 22 back to its original position, the user engages lower portion 30 of finger-actuated trigger 26 to slide the upper portion 28 back, opening port 58. This allows the pressurized fluid to flow from rear portion 46 of longitudinally extending hollow chamber 42 into the flow chamber 40. Since valve 38 is closed once stapling is finished, the pressurized fluid flows through release conduit 54 and out, into the environment, through port 58. Once the user removes his or her finger from lower portion 30 of finger-actuated trigger 26, the upper portion 28 is elastically biased to slide forward, again covering and sealing port 58, returning piston 22 to its initial position, such that the pneumatic actuator for dispensing surgical staples 10 may again be used, as in FIGS. 3A and 3B.

Since the front portion 44 of longitudinally extending hollow chamber 42 is not assumed to be free of fluid, an air port 62 is formed through the upper portion 14 of the housing 12 such that the front portion 44 of the longitudinally extending hollow chamber 42 is in fluid communication with an external environment. During compression of spring 24, and forward movement of piston 22 (FIGS. 3A and 3B), air is free to flow from front portion 44 into the external environment so that forward movement of piston 22 is not impeded. Similarly, during expansion of spring 24, and rearward movement of piston 22 (FIG. 3C), air is free to flow from the external environment into the front portion 44, such that rearward movement of piston 22 is not impeded.

It is to be understood that the pneumatic actuator for dispensing surgical staples is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A pneumatic actuator for dispensing surgical staples, comprising:
    a housing having an upper portion, a central portion and a lower portion, a longitudinally extending hollow chamber being formed in the upper portion of the housing, and a separate flow passage being formed in the central portion of the housing, whereby the lower portion of the housing is adapted for gripping by a hand of a user;
    a feed line at least partially mounted within the lower portion of the housing, the feed line being in direct selective fluid communication with the flow passage formed in the central portion of the housing, whereby the feed line is adapted for receiving pressurized fluid from an external source thereof;
    a first valve for selectively controlling the flow of the pressurized fluid from the feed line to the flow passage formed in the central portion of the housing;
    a spring-biased piston slidably received in the longitudinally extending hollow chamber, the piston dividing the longitudinally extending hollow chamber into a front portion and a rear portion, the piston providing a fluid-tight seal between the front portion and the rear portion, the flow passage being in open fluid communication with the rear portion of the longitudinally extending hollow chamber;
    a guide tube mounted to the front wall of the upper portion of the housing and extending longitudinally therefrom;
    a plunger rod secured to the piston and extending longitudinally to be at least partially received by, and slidably supported within, the guide tube;
    a second valve for selectively releasing the pressurized fluid from the rear portion of the longitudinally extending hollow chamber, wherein an upper portion of the second valve is slidably received within a valve chamber formed in the central portion of the housing; and
    a release conduit extending between the flow passage and the valve chamber, the release conduit being in fluid communication with the valve chamber through a port, the upper portion of the second valve selectively sealing the port,
    whereby the user selectively opens the first valve such that the pressurized fluid flows through the flow passage formed in the central portion of the housing and into the rear portion of the longitudinally extending hollow chamber to urge the piston forwardly therein, the forward movement of the piston pushing the plunger rod forwardly within the guide tube, the plunger rod being adapted for dispensing surgical staples from an attached surgical staple cartridge upon its forward movement.

2. The pneumatic actuator for dispensing surgical staples as recited in claim 1, wherein the second valve comprises a spring-biased finger-actuated trigger.

3. The pneumatic actuator for dispensing surgical staples as recited in claim 1, further comprising an air port formed through the upper portion of the housing, the front portion of the longitudinally extending hollow chamber being in fluid communication with an external environment through the air port.

4. The pneumatic actuator for dispensing surgical staples as recited in claim 1, further comprising a knob mounted on the lower portion of the housing, the knob being mechanically coupled to the first valve for selective opening and closing thereof.

* * * * *